(12) United States Patent
Swope

(10) Patent No.: US 6,380,267 B1
(45) Date of Patent: Apr. 30, 2002

(54) COMPOSITION AND METHOD FOR DECREASING NEUROLOGIC SYMPTOMATOLOGY

(76) Inventor: David M. Swope, 266 E. Crescent, Redlands, CA (US) 92373

( * ) Notice: Subject to any disclaimer, the term of this patent is extended or adjusted under 35 U.S.C. 154(b) by 17 days.

(21) Appl. No.: 09/731,362

(22) Filed: Dec. 5, 2000

Related U.S. Application Data

(63) Continuation of application No. PCT/US00/40901, filed on Sep. 13, 2000.
(60) Provisional application No. 60/153,586, filed on Sep. 13, 1999.

(51) Int. Cl.$^7$ ............................................. A61K 31/495
(52) U.S. Cl. .................. 518/252.16; 514/264; 514/265; 514/878; 514/879; 514/922
(58) Field of Search ............................ 514/252.16, 878, 514/879, 922

(56) References Cited

U.S. PATENT DOCUMENTS

| | | | |
|---|---|---|---|
| 3,961,060 A | 6/1976 | Fuxe | ........................... 424/253 |
| 5,712,282 A | 1/1998 | Iyo et al. | .................... 514/263 |

OTHER PUBLICATIONS

Kartzinel, Ronald et al., "Studies with bromocriptine: III. Concomitant administration of caffeine to patients with idiopathic parkinsonism." *Neurology*, 26:741–743 (Aug. 1976).

Shoulson, Ira et al., "Caffeine and the antiparkinsonian response to levodopa or piribedil," *Neurology*, 26::722–724 (Aug. 1975).

*Primary Examiner*—Frederick Krass
(74) *Attorney, Agent, or Firm*—David A. Farah; Sheldon & Mak

(57) ABSTRACT

A method of decreasing the signs or symptomatology in a patient with a neurologic condition or disease, or in a patient due to effects of exposure to an exogenous substance, such as a pharmaceutical agent, comprising selecting a patient having at least one sign or symptom selected from the group consisting of akinesia, bradykinesia, dyskinesias, gait disturbances, posture disturbances, rigid limbs, speech impairments and tremor and administering to the patient one or more than one effective doses of a phosphodiesterase inhibitor. A composition for decreasing the signs or symptomatology in a patient with a neurologic condition or disease, or in a patient due to effects of exposure to an exogenous substance, such as a pharmaceutical agent, the composition comprising an effective dose of one or more than one phosphodiesterase inhibitor combined with an effective dose of one or more than one additional pharmaceutical agent known to decrease signs or symptomatology in a patient with a neurologic condition or disease.

14 Claims, No Drawings

COMPOSITION AND METHOD FOR DECREASING NEUROLOGIC SYMPTOMATOLOGY

CROSS-REFERENCE TO RELATED APPLICATION

This Application takes priority from U.S. Provisional Patent Application No. 60/153,586, filed Sep. 13, 1999 and entitled "Method of Treating Neurologic Disease," and is a continuation of PCT Application PCT/US00/40901, filed Sep. 13, 2000 and entitled "Composition and Method for Decreasing Neurologic Symptomatology," the contents of which are incorporated in this disclosure by reference in its entirety.

BACKGROUND

Parkinson's Disease is a chronic, progressive, neurodegenerative disease of unknown cause. It is characterized by tremor, rigidity, slowness of movement and loss of postural reflexes. Disability from Parkinson's Disease results from the progressive impairment of mobility, as well as a form of dementia that often accompanies the disease.

Parkinson's Disease is more common in the elderly population, with a peak incidence between the ages of 55 and 60. The prevalence of Parkinson's Disease rises with increasing age. The disease is found worldwide and is estimated to affect 1% of the population of the United States.

The primary biochemical abnormality in Parkinson's Disease is a progressive loss of dopamine producing cells in the substantia nigra pars compacta area of the brain. These cells are located in the midbrain and project to the striatum. The cells synapse with striatal neurons using dopamine as a neurotransmitter. The loss of dopamine associated with the cell loss results in an imbalance in the inhibitory and excitatory circuitry in the basal ganglia, and this in turn results in impairment of movement characteristic of Parkinson's Disease.

There is no known cure for Parkinson's Disease, but several forms of symptomatic treatment are available. These treatments include medication and surgery.

The principal goal of symptomatic treatment is to restore the normal balance of neurotransmitters in the basal ganglia. The most potent medication available for the treatment of Parkinson's Disease is levodopa. Levodopa is the biochemical precursor to dopamine. It can be taken orally and it crosses the blood-brain barrier where it is taken up by dopaminergic cells in the brain. Levodopa is then converted to dopamine which is released.

Levodopa is very effective in ameliorating the symptoms of Parkinson's Disease during the early stages of the disease. However, potentially debilitating complications occur with chronic use of levodopa. For example, chronic use of levodopa causes its duration of action to progressively decrease, which causes patients to get cyclical fluctuations of Parkinson's Disease, symptoms known as "motor fluctuations." Additionally, chronic use of levodopa causes dyskinesias, which consists of random, purposeless movements or fixed postures. Such complications afflict approximately 50% of patients taking levodopa for more than five years.

The cause of levodopa complications is unknown but appears to be related to postsynaptic changes due to the pulsatile delivery of dopamine to the dopamine receptors. Dyskinesias are particularly difficult to treat. Treatments include adjustment in levodopa doses to optimize the patient's response. However, while decreasing the dose reduces the dyskinesias, it usually results in worsening of the underlying symptoms of Parkinson's Disease. Amantidine hydrochloride administration is effective in reducing the duration and severity of dyskinesias in some patients but it is associated with confusion and nausea, among other side effects. Further, surgical treatments such as pallidotomy and deep brain stimulation, are effective treatments for dyskinesias in some patients but these procedures are expensive and are associated with surgical complications themselves.

Therefore, there is a need for a new treatment for Parkinson's Disease that has fewer complications than current treatments. Further, there is a need for a new treatment for the complications associated with levodopa administration such as dyskinesias.

SUMMARY

A method of decreasing the signs or symptomatology in a patient with a neurologic condition or disease, or in a patient due to effects of exposure to an exogenous substance, such as a pharmaceutical agent. The method comprises selecting a patient having at least one sign or symptom selected from the group consisting of akinesia, bradykinesia, dyskinesias, gait disturbances, posture disturbances, rigid limbs, speech impairments and tremor. Then, the patient is administered one or more than one effective doses of a phosphodiesterase inhibitor such that the at least one sign or symptom improves.

In one embodiment, the patient selected is newly diagnosed with a neurologic disease or condition. In another embodiment, the patient selected has been taking medication or has had a surgical treatment and is experiencing dyskinesias. In a preferred embodiment, the signs or symptomatology are due to effects of exposure to levodopa.

In a preferred embodiment, the condition or disease is selected from the group consisting of dystonia, Huntington's Disease, multiple system atrophy, tardive dyskinesias and Tourette Syndrome. In a particularly preferred embodiment, the condition or disease is Parkinson's Disease.

In another preferred embodiment, the phosphodiesterase inhibitor is selected from the group consisting of caffeine, dipyridamole and theophylline. In a particularly preferred embodiment, the phosphodiesterase inhibitor is sildenafil.

In one embodiment, the method comprises administering a plurality of doses of the phosphodiesterase inhibitor. In a particularly preferred embodiment, the phosphodiesterase inhibitor is sildenafil and where the dose of sildenafil administered is between about 10 mg per day and about 200 mg per day, more preferably about 50 mg per day and most preferably about 25 mg per day. In another particularly preferred embodiment, the dose of the phosphodiesterase inhibitor is titrated for the particular patient until the patient receives the smallest dose that will maximally decrease the signs or symptomatology without creating unwanted side effects that outweigh the benefits of the phosphodiesterase inhibitor.

In another embodiment, the phosphodiesterase inhibitor is administered for between about one week and about twenty years, and more preferably for between about one year and about five years. In a preferred embodiment, the phosphodiesterase inhibitor is administered orally.

In one embodiment, the present invention is a composition for decreasing the signs or symptomatology in a patient with a neurologic condition or disease, or in a patient due to effects of exposure to an exogenous substance, such as a pharmaceutical agent. The composition comprises an effective dose of one or more than one phosphodiesterase inhibitor combined with an effective dose of one or more than one additional pharmaceutical agent known to decrease signs or symptomatology in a patient with a neurologic condition or disease. In a preferred embodiment, the phosphodiesterase inhibitor is sildenafil. In another preferred embodiment, the additional pharmaceutical agent is selected from the group consisting of an anticholinergic, a carbidopa/levodopa combination, a dopamine agonist, a catechol-o-methyl transferase inhibitor, levodopa, a monoamine oxidase type B inhibitor and an NMDA receptor antagonist. The composition can also comprise at least one substance selected from the group consisting of a binding agent, a coloring agent, an enteric coating and a flavoring agent.

The present invention also includes a method of decreasing the signs or symptomatology in a patient with a neurologic condition or disease, or in a patient due to effects of exposure to an exogenous substance, such as a pharmaceutical agent, the method comprising administering a composition according to the present invention.

In another embodiment of the present invention, there is provided a method of treating patients with Parkinson's Disease. The method comprises selecting a patient with Parkinson's Disease and administering one or more than one effective dose of a phosphodiesterase inhibitor such that the at least one sign or symptom improves. The one or more than one effective dose of a phosphodiesterase inhibitor can comprise administering a plurality of effective doses of the phosphodiesterase inhibitor.

In a preferred embodiment, the phosphodiesterase inhibitor is sildenafil. In a particularly preferred embodiment, the dose of sildenafil administered is between about 10 mg per day and about 200 mg per day, more preferably about 50 mg per day and most preferably about 25 mg per day.

In another embodiment of the present invention, there is provided a method of decreasing dyskinesias associated with a neurologic disease or with exposure to an exogenous substance, such as levodopa. The method comprises selecting a patient with a dyskinesia from a neurologic disease or from exposure to an exogenous substance, and administering one or more than one effective dose of a phosphodiesterase inhibitor, such as sildenafil.

DESCRIPTION

According to one embodiment of the present invention, there is provided a method of decreasing the signs or symptomatology in a patient with a neurologic condition or disease, such as Parkinson's Disease, or in a patient due to effects of exposure to an exogenous substance, such as a pharmaceutical agent. The method comprises selecting a patient with appropriate signs or symptomatology and administering one or more than one effective dose of a phosphodiesterase inhibitor, such as sildenafil.

According to another embodiment of the present invention, there is provided a composition for decreasing neurologic signs or symptomatology in a patient with a neurologic condition or disease, such as Parkinson's Disease, or in a patient due to effects of exposure to an exogenous substance, such as a pharmaceutical agent. The composition comprises one or more than one effective dose of a phosphodiesterase inhibitor, such as sildenafil, and one or more than one effective dose of another substance effective in decreasing neurologic signs or symptomatology.

As used in this disclosure, "signs or symptomatology" means either signs, or symptomatology, or a combination of signs and symptomatology.

According to one embodiment of the present invention, there is provided a method of decreasing neurologic signs or symptomatology in a patient with a neurologic condition or disease or in a patient due to effects of exposure to an exogenous substance. The method is particularly useful in decreasing neurologic signs or symptomatology related to movement and balance, such as akinesia, bradykinesia, gait disturbances, posture disturbances, rigid limbs, speech impairments and tremor, as well as dyskinesias associated with long term exposure to pharmaceutical agents such as levodopa. The method is particularly useful in decreasing neurologic signs or symptomatology due to diseases and conditions such as Parkinson's Disease, tardive dyskinesias, Tourette Syndrome, Huntington's Disease, multiple system atrophy and dystonia, or subsequent to viral infections, or due to exposure to an exogenous substance such to MPTP (1-methyl-4-phenyl-1,2,3,6-tetrahydropyridine) or to pharmaceutical agents used to treat neurologic diseases, such as levodopa. The method can also be used to treat other diseases and conditions which have similar signs or symptomatology as Parkinson's Disease.

The method comprises, first, selecting a patient having appropriate signs or symptomatology. The patient can be newly diagnosed with a neurologic disease or condition, or have been previously diagnosed with a neurologic disease or condition. In a preferred embodiment, the patient has been previously diagnosed with a neurologic disease or condition, has been taking medication or has had a surgical treatment for the neurologic disease or condition, and has still experienced signs or symptomatology or has had unwanted side effects of the medication or surgery, such as dyskinesias.

The patient is then administered one or more than one effective dose of a phosphodiesterase inhibitor. In a preferred embodiment, the phosphodiesterase inhibitor is selected from the group consisting of caffeine, dipyridamole and theophylline. In a particularly preferred embodiment, the phosphodiesterase inhibitor is sildenafil (Viagra®, available from Pfizer, Inc., New York, N.Y. US).

In another preferred embodiment, the method includes administering a plurality of doses of the phosphodiesterase inhibitor. In a particularly preferred embodiment, the phosphodiesterase inhibitor is sildenafil and the dose of sildenafil administered is between about 10 mg per day and about 200 mg per day, and more preferably the dose is 25 mg per day. However, as will be understood by those with skill in the art with reference to this disclosure, the dose should be titrated for the particular patient until the patient receives the smallest dose that will maximally decrease the signs or symptomatology without creating unwanted side effects that outweigh the benefits of the phosphodiesterase inhibitor.

In another preferred embodiment, the phosphodiesterase inhibitor is administered for between about one week and about twenty years. In a particularly preferred embodiment, the phosphodiesterase inhibitor is administered for between about one year and about five years.

In a preferred embodiment, the phosphodiesterase inhibitor is administered orally, though other routes of administration are also within the scope of this invention, including administration by skin patch, subcutaneous injection, inhaled preparations and direct intravenous administration.

In a particularly preferred embodiment, the method of the present invention comprises administering a plurality of doses of a composition according to the present invention. The composition comprises an effective dose of one or more than one phosphodiesterase inhibitor, such as sildenafil, and an effective dose of one or more than one other pharmaceutical agents that is effective in decreasing neurologic signs or symptomatology. In a particularly preferred embodiment, the one or more than one other pharmaceutical agents is an agent know to decrease dyskinesias associated with a neurologic disease or associated with the exposure to an exogenous substance.

According to another embodiment of the present invention, there is provided a composition for decreasing the signs or symptomatology in a patient with a neurologic condition or disease, such as Parkinson's Disease, or in a patient due to effects of exposure to an exogenous substance, such as a pharmaceutical agent. The composition comprises an effective dose of one or more than one phosphodiesterase inhibitor combined with an effective dose of one or more than one additional pharmaceutical agent known to decrease signs or symptomatology in a patient with a neurologic condition or disease. In a preferred embodiment, the additional pharmaceutical agent is selected from the group consisting of an anticholinergic, a carbidopa/levodopa combination, a dopamine agonist, a catechol-o-methyl transferase inhibitor, levodopa, a monoamine oxidase type B inhibitor and an NMDA receptor antagonist. Examples of suitable anticholinergics are trihexyphenidyl (available as Artane® from Lederle Pharmaceutical Division, Pearl River, N.Y. US), and benztropine (available as Cogentin® from Merck and Co., West Point, Pa. US). Examples of suitable carbidopa/levodopa combinations are Sinemet® and Sinemet® CR, (both from Merck and Co., West Point, Pa. US). Examples of suitable dopamine agonists are pramipexole (available as Mirapex® from Pharmacia and Upjohn Co., Kalamazoo Mich. US), ropinerole (available as Requip® from SmithKline Beecham Pharmaceuticals, Philadelphia Pa. US), pergolide (available as Permax® from Athena Neurosciences Inc., San Francisco Calif. US) and bromocriptine (available as Parlodel® from Novartis Pharmaceuticals, Inc., East Hanover, N.J. US). Examples of suitable catechol-o-methyl transferase inhibitors are tolcapone (available as Tasmar® from Roche Pharmaceuticals, Nutley, N.J. US) and entacapone (available as Comtan® from Novartis Pharmaceuticals, Inc., East Hanover, N.J. US). An example of a suitable monoamine oxidase type B inhibitor is selegiline (available as Eldepryl® from Somerset Pharmaceuticals, Inc., Tampa, Fla. US). An example of a suitable NMDA receptor antagonist is amantadine (available as Symmetrel® from Endo Pharmaceuticals Inc., Chadds Ford, Pa. US).

In a preferred embodiment, the composition comprises effective doses of a plurality of phosphodiesterase inhibitors, or effective doses of a plurality of other pharmaceutical agents, or both effective doses of a plurality phosphodiesterase inhibitors and effective doses of a plurality of other pharmaceutical agents.

In another preferred embodiment, the effective dose of the one or more than one other pharmaceutical agents is the same as the dose that would be given if the pharmaceutical agent was not combined with the phosphodiesterase inhibitor. In a particularly preferred embodiment, the effective dose of the one or more than one other pharmaceutical agent is between about one tenth and about ninth tenths of the dose that would be given if the pharmaceutical agent was not combined with the phosphodiesterase inhibitor. In another particularly preferred embodiment, the effective dose of the one or more than one other pharmaceutical agent is about one half of the dose that would be given if the pharmaceutical agent was not combined with the phosphodiesterase inhibitor.

As will be understood by those with skill in the art with reference to this disclosure, the composition of the present invention can also comprise one or more than one additional substances, such a binding agent, a coloring agent, an enteric coating and a flavoring agent. The composition is preferably configured to be administered orally. However, it can also be configured to be administered by skin patch, subcutaneous injection, inhaled preparations or direct intravenous administration, among other routes, as will be understood by those with skill in the art with reference to this disclosure.

EXAMPLE I

METHOD FOR DECREASING NEUROLOGIC SYMPTOMATOLOGY

A 60 year old, Caucasian, male patient who had Parkinson's Disease for twelve years and who suffered from severe dyskinesia affecting all his extremities and his head and neck for five years was treated with the method for decreasing neurologic symptomatology according to the present invention. Before beginning treatment according to the present method, the patient was taking 700 mg of levodopa per day. The patient was initially treated with 50 mg of sildenafil per day. During treatment, his dyskinesias were significantly reduced and his dose of sildenafil was decreased to 25 mg of sildenafil and his dose of levodopa was reduced to between 300 and 400 mg per day. The patient's signs and symptoms of Parkinson's Disease remain significantly improved after more than one year of treatment according to the present method.

EXAMPLE II

METHOD FOR DECREASING NEUROLOGIC SYMPTOMATOLOGY

A 55 year old, Caucasian, male patient who had Parkinson's Disease for fifteen years and who suffered from tremor at rest and gait disturbance was treated with the method for decreasing neurologic symptomatology according to the present invention. Before beginning treatment according to the present method, the patient was taking levodopa 500 mg per day. The patient was initially treated with 25 mg of sildenafil per day. After five months of treatment, his tremor had ceased and his gait disturbance had improved significantly and his dose of sildenafil was increased to 25 mg three times per day and his dose of levodopa was decreased to 250 mg per day. The patient's signs and symptoms of Parkinson's Disease remain significantly improved after more than seven months of treatment.

EXAMPLE III

METHOD FOR DECREASING NEUROLOGIC SYMPTOMATOLOGY

Seven additional patients with Parkinson's Disease and dyskinesias were treated with sildenafil at a dose of 25 mg per day in addition to their usual Parkinson's Disease medications. The patents were all Caucasian and ranged in age from between 55 to 70 years. Four of the patients were men and three were women. Five of the seven patients had significant improvement in their dyskinesias using a dose the 25 mg per day. None of the patients demonstrated any significant side effects of sildenafil treatment or any worsening of their Parkinson's Disease symptoms, though one did report facial flushing.

Although the present invention has been discussed in considerable detail with reference to certain preferred embodiments, other embodiments are possible. Therefore, the scope of the appended claims should not be limited to the description of preferred embodiments contained herein.

I claim:

1. A method for decreasing signs or symptomology of Parkinson's disease comprising:
   a) selecting a patient having Parkinson's disease; and
   b) administering to the patient an effective amount of sildenafil.

2. The method of claim 1, wherein the patient has been newly diagnosed with Parkinson's disease.

3. The method of claim 1, wherein a plurality of doses of sildenafil are administered.

4. The method of claim 1, wherein between about 10 mg/day and 200 mg/day sildenafil are administered.

5. The method of claim 1, wherein about 50 mg/day sildenafil is administered.

6. The method of claim 1, wherein about 25 mg/day sildenafil is administered.

7. The method of claim 1, wherein administration is titrated for a particular patient to minimize the effective dose and unwanted side effects.

8. The method of claim 1, wherein administration occurs over a time period ranging from about one week to about twenty years.

9. The method of claim 1, wherein administration occurs over a time period ranging from about one year to about five years.

10. The method of claim 1, wherein administration is oral.

11. A composition for decreasing signs or symptomology of Parkinson's disease, said composition comprising:
    a) an effective amount of sildenafil; and
    b) an effective amount of a different agent which decreases signs or symptomology of Parkinson's disease when administered to patients having said disease.

12. The composition of claim 11, wherein said different agent is selected from the group consisting of anticholinergics, carbidopa/levodopa combinations, dopamine agonists, catechol-o-methyl transferase inhibitors, levodopa, monoamine oxidase type-B inhibitors, and NMDA receptor antagonists.

13. The composition of claim 11, wherein said different agent is selected from the group consisting of amantadine, benzotropine, bromocriptine, entacapone, pergolide, pramipexole, ropinerole, selegine, tolcapone and trihexyphenidyl.

14. The composition of claim 11, additionally containing a binding agent, coloring agent, enteric coating or flavoring agent.

* * * * *

UNITED STATES PATENT AND TRADEMARK OFFICE
Certificate

Patent No. 6,380,267 B1            Patented: April 30, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: David M. Swope, Redlands, CA; and Dale E. Neldner, Barstow, CA.

Signed and Sealed this First Day of April 2003.

MARIANNE SEIDEL
*Supervisory Patent Examiner*
Art Unit 1614